(12) United States Patent
Suehara et al.

(10) Patent No.: US 12,016,691 B2
(45) Date of Patent: Jun. 25, 2024

(54) MONITORING SYSTEM AND OXYGEN MEASUREMENT SYSTEM

(71) Applicant: TERUMO KABUSHIKI KAISHA, Tokyo (JP)

(72) Inventors: Satoru Suehara, Kanagawa (JP); Akihiro Takahashi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 745 days.

(21) Appl. No.: 16/584,997

(22) Filed: Sep. 27, 2019

(65) Prior Publication Data

US 2020/0022638 A1 Jan. 23, 2020

Related U.S. Application Data

(63) Continuation of application No. PCT/JP2018/009546, filed on Mar. 12, 2018.

(30) Foreign Application Priority Data

Mar. 30, 2017 (JP) ................................ 2017-066659

(51) Int. Cl.
*A61B 5/20* (2006.01)
*A61B 5/00* (2006.01)
*A61B 5/145* (2006.01)

(52) U.S. Cl.
CPC .......... *A61B 5/208* (2013.01); *A61B 5/14507* (2013.01); *A61B 5/201* (2013.01);
(Continued)

(58) Field of Classification Search
CPC .. A61B 5/20–208; A61B 5/145–14507; A61B 5/1455–1459;
(Continued)

(56) References Cited

U.S. PATENT DOCUMENTS 3,874,850 A * 4/1975 Sorensen ........... G01N 33/4925
436/163
2005/0228305 A1* 10/2005 Nagata ................... A61B 5/349
600/509

(Continued)

FOREIGN PATENT DOCUMENTS

| CN | 203829120 U | 9/2014 |
| JP | 2739880 B2 | 3/1995 |

(Continued)

OTHER PUBLICATIONS

Machine English Translation of WO 2017/21323 7A1, patents.google.com, 24 pages, printed on Sep. 19, 2022 (Year: 2022).*

(Continued)

*Primary Examiner* — Matthew Kremer
(74) *Attorney, Agent, or Firm* — Buchanan Ingersoll & Rooney PC

(57) ABSTRACT

A monitoring system which constitutes an oxygen measurement system includes: an oxygen partial pressure calculation unit that calculates an oxygen partial pressure in urine based on an output signal from the oxygen measurement device; a monitor that displays the oxygen partial pressure calculated by the oxygen partial pressure calculation unit; and a display control unit that changes a format of display of the oxygen partial pressure displayed by the monitor according to the flow rate of urine acquired based on the output signal from the oxygen measurement device.

18 Claims, 12 Drawing Sheets

(52) U.S. Cl.
CPC ............ *A61B 5/204* (2013.01); *A61B 5/6852* (2013.01); *A61B 5/7271* (2013.01); *A61B 5/743* (2013.01)

(58) Field of Classification Search
CPC ...... A61B 5/6852–6853; A61B 5/7271; A61B 5/743; A61B 5/01; A61B 5/742
See application file for complete search history.

(56) References Cited

U.S. PATENT DOCUMENTS

| | | | |
|---|---|---|---|
| 2006/0020225 A1* | 1/2006 | Gerber | A61B 5/002 600/549 |
| 2008/0103408 A1 | 5/2008 | Denton et al. | |
| 2010/0286559 A1* | 11/2010 | Paz | A61B 5/412 600/581 |
| 2010/0317931 A1* | 12/2010 | Sarkela | A61B 5/72 600/300 |
| 2011/0218406 A1* | 9/2011 | Hussain | A61B 5/14551 600/300 |
| 2013/0253294 A1* | 9/2013 | Schabbach | A61B 5/157 600/345 |
| 2014/0073900 A1* | 3/2014 | Wood | A61B 5/14551 600/407 |
| 2016/0066842 A1* | 3/2016 | Kokkoneva | A61B 5/742 600/479 |
| 2016/0183819 A1* | 6/2016 | Burnett | A61B 5/14507 600/561 |
| 2018/0168450 A1* | 6/2018 | Soosalu | A61B 5/742 |
| 2022/0152302 A1* | 5/2022 | Halpert | A61B 5/20 |

FOREIGN PATENT DOCUMENTS

| | | | | |
|---|---|---|---|---|
| JP | 2006317224 A | 11/2006 | | |
| JP | 2009523463 A | 6/2009 | | |
| WO | WO-2015105916 A1 * | 7/2015 | ............ | A61B 5/208 |
| WO | 2015/145424 A1 | 10/2015 | | |
| WO | WO-2017213237 A1 * | 12/2017 | ............ | A61B 5/00 |

OTHER PUBLICATIONS

International Search Report (PCT/ISA/210) dated May 20, 2018, by the Japanese Patent Office as the International Searching Authority for International Application No. PCT/JP2018/009546.

An English Translation of the International Search Report (Form PCT/ISA/210) and the Written Opinion of the International Searching Authority (Form PCT/ISA/237) dated May 22, 2018, by the Japanese Patent Office in corresponding International Application No. PCT/JP2018/009546. (6 pages).

U.S. Appl. No. 16/584,979, filed Sep. 27, 2019, Suehara et al.

Office Action (The First Office Action) dated Nov. 25, 2021, by the State Intellectual Property Office of People's Republic of China in corresponding Chinese Patent Application No. 201880022822.6 and an English Translation of the Office Action. (10 pages).

* cited by examiner

MONITORING SYSTEM AND OXYGEN MEASUREMENT SYSTEM

CROSS-REFERENCES TO RELATED APPLICATIONS

This application is a continuation of International Application No. PCT/JP2018/009546 filed on Mar. 12, 2019, which claims priority to Japanese Patent Application No. 2017-066659 filed on Mar. 30, 2019, the entire content of which is incorporated herein by reference.

FIELD OF THE INVENTION

The present invention generally relates to a monitoring system provided in a urethral catheter, and an oxygen measurement system.

BACKGROUND DISCUSSION

Japanese Patent No. 2739880 discloses an example of an oxygen measurement device in which an oxygen sensor is inserted into the bladder and indwelled through the urine flow lumen of a urethral catheter. This oxygen measurement device is a device that detects oxygen partial pressure in the epithelial wall and monitors it by leading-out an oxygen sensor main body of an oxygen sensor from a urethral catheter port formed at a distal portion of the urethral catheter, and bringing the oxygen sensor main body into contact with the epithelial wall of the bladder.

SUMMARY

Studies are being conducted to predict a state of the kidneys by measuring oxygen partial pressure in urine, assuming that an oxygen status in urine reflects an oxygen status of kidney tissue. In a case of predicting such a state of the kidneys, it is important to measure an oxygen partial pressure in urine which has just been excreted from the kidneys, that is, urine which is stably flowing. However, by merely measuring and monitoring the oxygen partial pressure in urine, it is not easy to confirm whether or not the measured oxygen partial pressure is an oxygen partial pressure in urine that is flowing stably.

The monitoring system and oxygen measurement system disclosed here are able to confirm whether or not a measured oxygen partial pressure is an oxygen partial pressure which is in urine flowing stably and which appropriately reflects a state of the kidneys is easy.

The monitoring system is connectable to an oxygen measurement device that includes sensors to be exposed to urine (urine obtained from a living body) and which operates to calculate an oxygen partial pressure in urine and a flow rate of urine. The monitoring system comprises: an oxygen partial pressure calculation unit connected to a first one of the sensors of the oxygen measurement device when the monitoring system is connected to the oxygen measurement device to receive an output signal from the first sensor and to calculate, for display on the monitor, an oxygen partial pressure in the urine based on the output signal from the first sensor of the oxygen measurement device. A flow rate calculation unit is connected to a second one of the sensors of the oxygen measurement device when the monitoring system is connected to the oxygen measurement device to receive an output signal from the second sensor and to calculate a flow rate of the urine based on the output signal from the second sensor of the oxygen measurement device. A display control unit is connected to a monitor during operation of the monitoring system and controls a format of a display of the oxygen partial pressure on the monitor so that the format of the display of the oxygen partial pressure on the monitor varies based on the calculated flow rate of urine, to thereby allow a user of the monitoring system to confirm whether or not the oxygen partial pressure is an oxygen partial pressure acquired in a state that appropriately reflects a state of the kidneys.

According to such a configuration, by looking at the format of display of the oxygen partial pressure displayed on the monitor, it is possible to easily confirm whether or not a measured oxygen partial pressure is an oxygen partial pressure which is in urine flowing stably and which appropriately reflects a state of the kidneys.

The monitoring system further includes a flow rate determination unit that determines whether or not the flow rate of the urine acquired based on the output signal from the first sensor of the oxygen measurement device is equal to or more than a predetermined value. The display control unit controls the format of the display of the oxygen partial pressure so that the oxygen partial pressure is displayed on the monitor in a first display format when the flow rate determination unit determines that the flow rate of the urine is equal to or higher than the predetermined value, and controls the format of the display of the oxygen partial pressure so that the oxygen partial pressure is displayed on the monitor in a second display format visually different from the first display format when the flow rate determination unit determines that the flow rate of the urine is less than the predetermined value.

According to such a configuration, in a case where the monitor displays the oxygen partial pressure in the first display format, it is possible to easily confirm that the measured oxygen partial pressure is an oxygen partial pressure in urine flowing at a flow rate equal to or higher than a predetermined value. In addition, in a case where the monitor displays the oxygen partial pressure in the second display format, it is possible to easily confirm that the measured oxygen partial pressure is an oxygen partial pressure in urine at a flow rate less than a predetermined value. Accordingly, it is possible to easily confirm whether or not the oxygen partial pressure is an oxygen partial pressure which is acquired in a state that appropriately reflects a state of the kidneys.

The monitoring system further includes a flow rate determination unit that determines whether or not the flow rate of the urine acquired based on the output signal from the first sensor of the oxygen measurement device is equal to or more than a predetermined value. The display control unit controls the format of the display of the oxygen partial pressure so that the oxygen partial pressure is displayed on the monitor when the flow rate determination unit determines that the flow rate of urine is equal to or higher than the predetermined value, and controls the format of the display of the oxygen partial pressure so that the oxygen partial pressure is not displayed on the monitor when the flow rate determination unit determines that the flow rate of urine is less than the predetermined value.

According to such a configuration, in a case where the monitor displays the oxygen partial pressure, it is possible to easily confirm that the measured oxygen partial pressure is an oxygen partial pressure in urine flowing at a flow rate equal to or higher than a predetermined value. Accordingly, it is possible to easily confirm whether or not the oxygen partial pressure is an oxygen partial pressure which is acquired in a state that appropriately reflects a state of the kidneys.

In the monitoring system, the display control unit may allow the monitor to display a graph indicating a temporal change of oxygen partial pressure.

According to such a configuration, it is possible to easily confirm a temporal change of oxygen partial pressure in urine. Accordingly, it is possible to easily confirm whether a state of the kidneys is in better state as compared to the previous state, and it is possible to perform interventions such as treatment and its adjustment at appropriate timing as needed.

In the monitoring system, the oxygen partial pressure calculation unit may calculate the oxygen partial pressure in urine corrected by a temperature in the urine acquired based on the output signal from a further sensor of the oxygen measurement device.

According to such a configuration, it is possible to display a more accurate oxygen partial pressure in urine which has been temperature-corrected on the monitor.

The monitoring system further includes a urine volume calculation unit connected to the second one of the sensors of the oxygen measurement device when the monitoring system is connected to the oxygen measurement device to receive an output signal from the second sensor and to calculate, for display on the monitor, a urine volume based on the output signal from the second sensor of the oxygen measurement device. A urine volume determination unit determines whether or not the urine volume calculated by the urine volume calculation unit matches a predetermined urine volume condition, and the display control unit displays the predetermined urine volume condition on the monitor when the urine volume determination unit determines that the urine volume matches the urine volume condition.

According to such a configuration, it is possible to easily confirm whether or not the urine volume matches a predetermined urine volume condition (for example, whether or not the urine volume is excessively small). Accordingly, it is possible to easily confirm whether a state of the kidneys is in better state as compared to the previous state, and it is possible to perform interventions such as treatment and its adjustment at appropriate timing as needed.

An oxygen measurement system comprises: a urethral catheter that includes a urine flow lumen in which urine circulates; an oxygen sensor that is mounted along the urine flow lumen in the urethral catheter and that outputs an output signal used to calculate an oxygen partial pressure in the urine circulating in the urine flow lumen of the urethral catheter; a flow rate sensor that is mounted along the urine flow lumen in the urethral catheter and that outputs an output signal used to calculate a flow rate of the urine circulating in the urine flow lumen of the urethral catheter; an oxygen partial pressure calculation unit that calculates the oxygen partial pressure in the urine circulating in the urine flow lumen of the urethral catheter based on the output signal output from the oxygen sensor; a flow rate calculation unit that calculates a flow rate of the urine circulating in the urine flow lumen of the urethral catheter based on the output signal output from the flow rate sensor; a monitor that displays the oxygen partial pressure calculated by the oxygen partial pressure calculation unit; and a display control unit that is connected to the monitor and that changes a format of a display of the oxygen partial pressure on the monitor so that the format of the display of the oxygen partial pressure on the monitor varies based on the flow rate of the urine.

According to such a configuration, it is possible to obtain an oxygen measurement system that exhibits the same effect as the monitoring system described above.

According to another aspect, a method comprises positioning a distal portion of an elongated urethral catheter in a bladder of a living body, introducing urine from the bladder of the living body into a lumen of the elongated urethral catheter; calculating an oxygen partial pressure in the urine in the lumen of the elongated urethral catheter based on an output signal of a first sensor that is contacted by the urine in the lumen of the elongated urethral catheter; calculating a flow rate of the urine in the lumen of the elongated urethral catheter based on an output signal from a second sensor that is contacted by the urine in the lumen of the elongated urethral catheter; and controlling display of the calculated oxygen partial pressure on the monitor, wherein the controlling of the display of the calculated oxygen partial pressure comprises varying a format of the display of the oxygen partial pressure on the monitor based on the calculated flow rate of the urine.

The monitoring system and method disclosed here are implemented so that the format of display of an oxygen partial pressure on a monitor is changed according to a flow rate of urine acquired based on an output signal from an oxygen measurement device, so that by looking at the format of display of the oxygen partial pressure on the monitor, it is possible for the user to easily confirm whether or not the measured oxygen partial pressure is an oxygen partial pressure in urine flowing stably. Accordingly, it is possible to easily confirm whether or not the oxygen partial pressure is an oxygen partial pressure which is acquired in a state that appropriately reflects a state of the kidneys. In addition, it is possible to easily confirm whether a state of the kidneys is in better state as compared to the previous state, and it is possible to perform interventions such as treatment and its adjustment at appropriate timing as needed.

DETAILED DESCRIPTION

Set forth below with reference to the accompanying drawings is a detailed description of embodiments of a monitoring system and an oxygen measurement system representing examples of the inventive monitoring system and an oxygen measurement system disclosed here.

An oxygen measurement system 12 according to one embodiment disclosed here by way of example is for measuring an oxygen partial pressure (oxygen concentration) in urine excreted from kidneys into a bladder 140 in order to predict or ascertain the condition of the kidneys.

Figure 1:
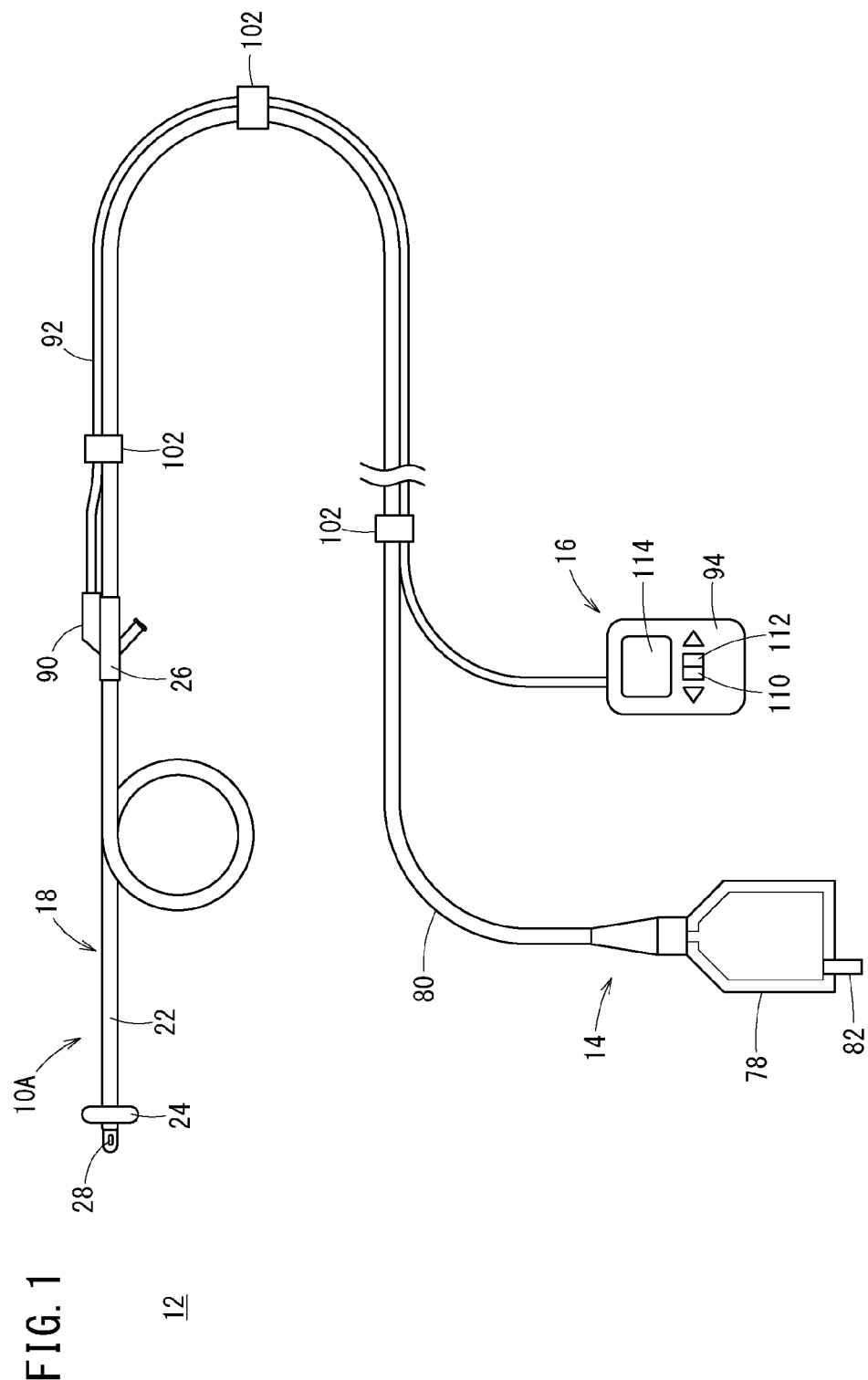
FIG. 1 is a schematic view showing a schematic configuration of an oxygen measurement system including an oxygen measurement device according to one disclosed embodiment.
Figure 2:
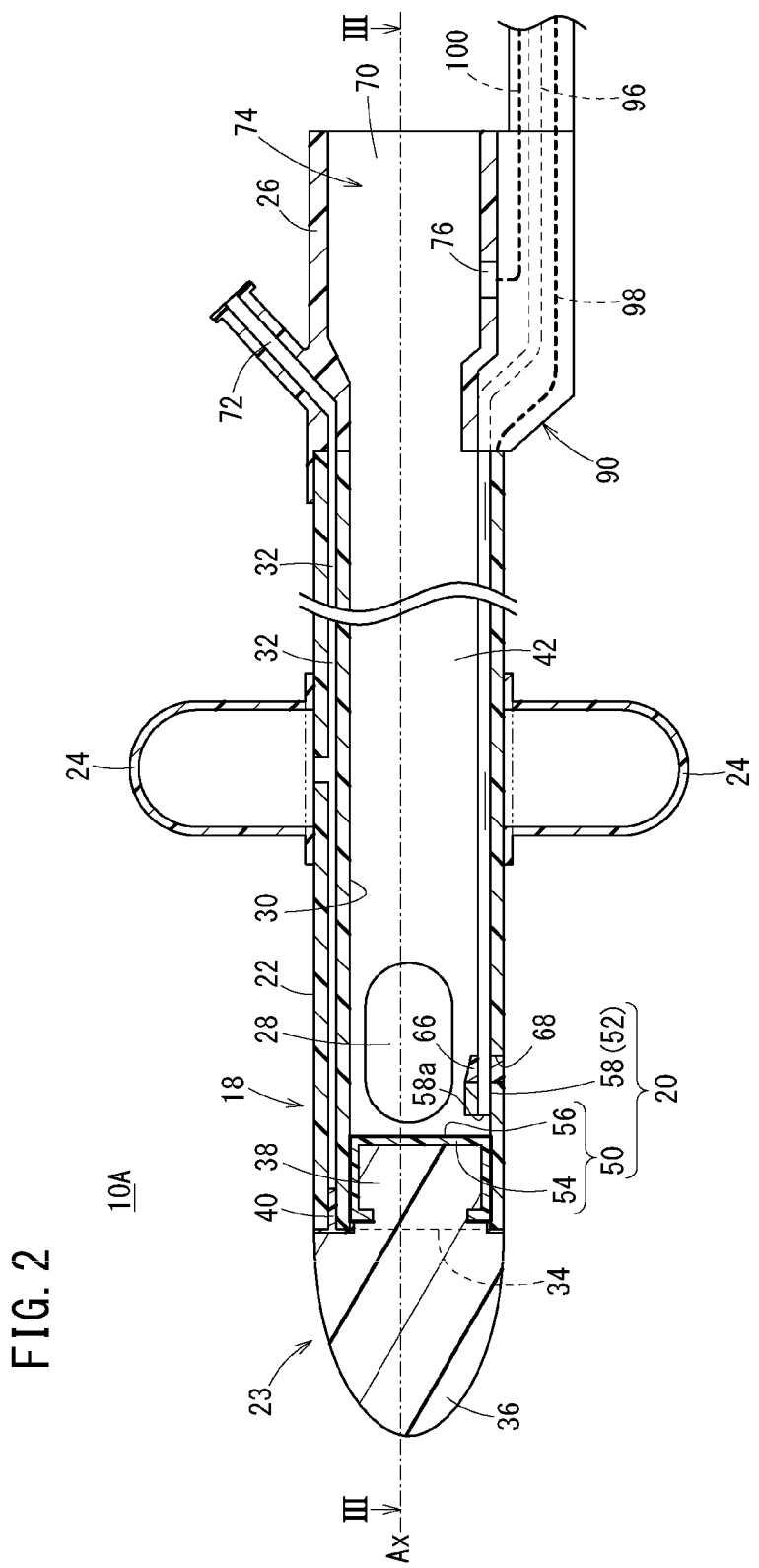
FIG. 2 is a partially omitted longitudinal cross-sectional view of the oxygen measurement device shown in FIG. 1.

As shown in FIG. 1, the oxygen measurement system 12 includes an oxygen measurement device 10A comprised of a urethral catheter 18, a urine collection bag 14 (a urine collection container), and a monitoring system 16. In the following description, the right side of the urethral catheter 18 in FIG. 2 is referred to as the "proximal side" (proximal end) and the left side of the urethral catheter 18 is referred to as the "distal side" (distal end). This same nomenclature applies to the other drawings.

As shown in FIGS. 1 and 2, the oxygen measurement device 10A includes a urethral catheter 18 and an oxygen sensor 20. The urethral catheter 18 is a medical device that is indwelled in the living body at the time of use and directs or conveys the urine in the bladder 140 into the urine collection bag 14 disposed outside the body. The urethral catheter 18 includes a flexible hollow elongated shaft 22, a closing portion 23 (distal end cap) provided at the distal end of the shaft 22, a balloon 24 provided at the distal portion of the shaft 22, and a hub 26 provided at the proximal portion of the shaft 22.

The shaft 22 is a thin and long tube. The shaft 22 has adequate flexibility and adequate rigidity to allow the distal portion of the urethral catheter 18 to pass smoothly into the bladder 140 through a urethra 144. Examples of constituent materials from which the shaft 22 may be fabricated include rubbers such as silicone or latex, other elastomers, vinyl chloride, polyurethane, plastic tubes, and the like.

Figure 3:
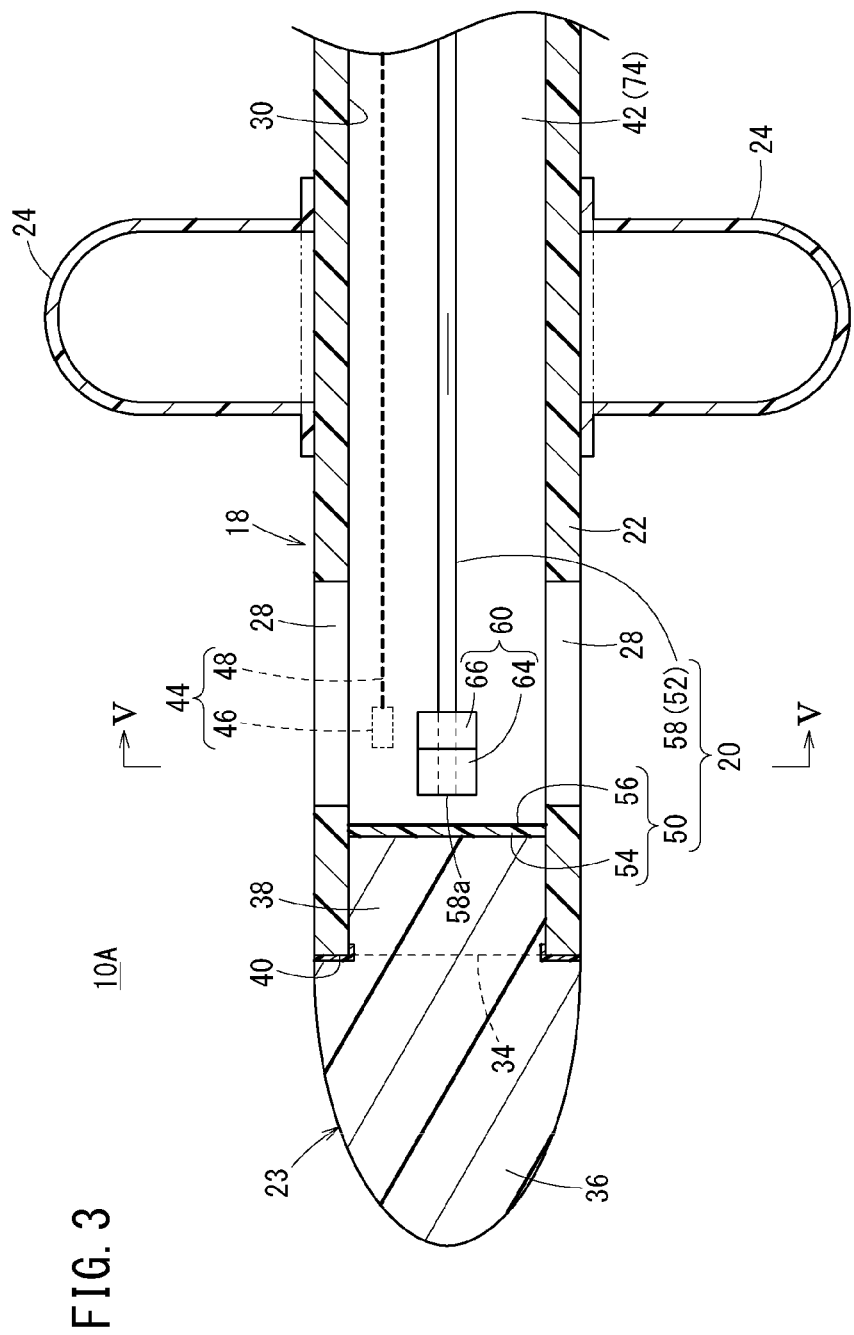
FIG. 3 is a partially omitted longitudinal cross-sectional view taken along the line III-III in FIG. 2.

As shown in FIGS. 2 and 3, the shaft 22 includes two urethral catheter ports 28 (through holes in the wall of the shaft 22) which allow urine in the bladder 140 to flow into the shaft 22; a lumen 30 communicating with the urethral catheter ports 28 and extending the entire length of the shaft 22; and an inflation lumen 32 for circulating the inflation fluid of the balloon 24. The lumen 30 is surrounded by the wall constituting the elongated shaft 22.

Each of the urethral catheter ports 28 opens at a position distal of the balloon 24 on the outer peripheral surface of the shaft 22. The two urethral catheter ports 28 are provided at positions facing each other (diametrically opposed). Each of the urethral catheter port 28 is an elongated hole extending in the longitudinal direction of the shaft 22 as generally shown in FIGS. 1-3. Specifically, each urethral catheter port 28 is formed in the shape (shape close to an ellipse) in which each short side of the rectangle protrudes outward in an arc shape (refer to FIG. 2). The shape, size, position and number of the urethral catheter port 28 can be optionally set.

Figure 4:
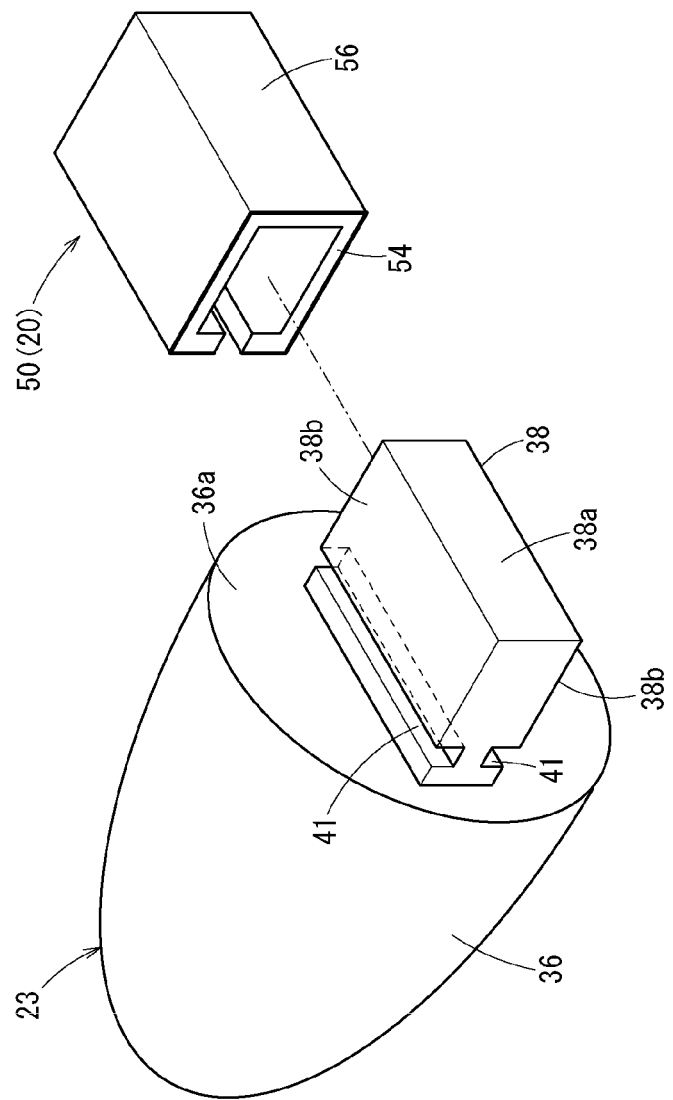
FIG. 4 is a perspective view of a closing portion and an oxygen sensor main body shown in FIG. 2.
Figure 5:
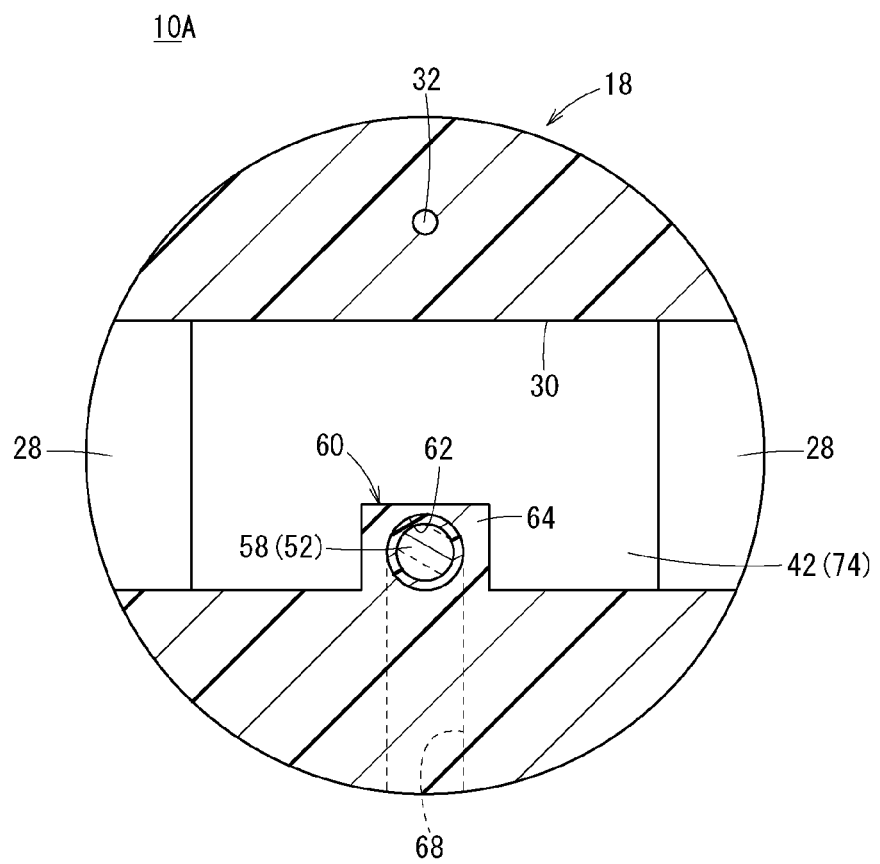
FIG. 5 is a transverse cross-sectional view taken along the line V-V of FIG. 3.

A distal end opening portion 34 of the lumen 30 is formed at the distal end surface of the shaft 22. The distal end opening portion 34 of the lumen 30 is closed by the closing portion 23. The closing portion 23 may be made of the same material as the shaft 22. As shown in FIG. 2, FIG. 3, and FIG. 5, the closing portion 23 includes a distal end enlarged portion 36 that tapers in outer dimension toward the distal end of the enlarged portion 36 (i.e., in a direction away from the shaft 22), and a protruding portion 38 that protrudes in the proximal direction from a proximal surface 36a (refer to FIG. 4) of the distal end enlarged portion 36 and that is fluid-tightly fitted to the distal end opening portion 34 of the lumen 30. An outer surface of the distal end enlarged portion 36 is configured as a partial curved surface of a spheroid. The proximal surface 36a of the distal end enlarged portion 36 is a flat shape. The protruding portion 38 possesses a rectangular parallelepiped shape.

In FIG. 2 and FIG. 3, the closing portion 23 may be fixed to the shaft 22 by an adhesive 40. The adhesive 40 may be injected between the proximal surface 36a of the distal end enlarged portion 36, and the distal end surface of the shaft 22; and between the protruding portion 38, and the wall surface constituting the distal end opening portion 34 of the lumen 30. A latching groove 41 is formed across the entire width on each of two side surfaces 38b located on both sides in a height direction (short direction) of a protruding end surface 38a of the protruding portion 38 (refer to FIG. 4).

A portion of the lumen 30 of the shaft 22 that is proximal of the closing portion 23 functions as a urethral catheterization lumen 42. The urethral catheterization lumen 42 is provided such that the axis Ax of the shaft 22 is located in the urethral catheterization lumen. According to one embodiment, the urethral catheterization lumen 42 has a square cross section (refer to FIG. 5). However, the cross section of the urethral catheterization lumen 42 may adopt any shape.

As shown in FIG. 3, a temperature sensor 44 is embedded in the wall of the shaft 22. The temperature sensor 44 has a temperature sensor main body or sensor for detecting temperature 46 (temperature probe) for detecting the temperature in the bladder 140, and a temperature transmission unit 48 electrically connected to the temperature sensor main body 46. The temperature sensor main body 46 is at the same position as the urethral catheterization port 28 in the axial direction of the shaft 22. That is, the temperature sensor main body 46 is at the same axial position as the urethral catheter ports 28, meaning the temperature sensor main body 46 and the urethral catheter ports 28 axial overlap one another as shown in FIG. 3. The temperature sensor main body 46 includes a thermocouple, a resistance temperature detector, or a thermistor. The temperature sensor 44 can detect a temperature of urine in the bladder 140. The temperature sensor main body 46 may be at a position shifted from the urethral catheter port 28 in the axial direction of the shaft 22 toward the distal side or the proximal side. In addition, the temperature sensor main body 46 may be disposed in the urethral catheterization lumen 42. In this case, a temperature of the urine circulating in the urine flow lumen 74 can be accurately detected.

The oxygen sensor 20 is provided in the urethral catheterization lumen 42. The oxygen sensor 20, which is configured as a so-called fluorescent (optical) oxygen sensor 20, includes an oxygen sensor main body 50, which is capable of detecting oxygen in urine, and an oxygen transmission unit 52 (optical fiber 58) provided separately from the oxygen sensor main body 50 and disposed in the urethral catheterization lumen 42. The oxygen sensor 20 is fixed to the urethral catheter 18 so that the oxygen sensor main body 50 contacts urine circulating in the urethral catheterization lumen.

The oxygen sensor main body 50 has a substrate 54 (base part) and a phosphor 56 applied to substantially the entire surface of one side of the substrate 54. The substrate 54 is made of a material that can transmit excitation light from the optical fiber 58 and fluorescence from the phosphor 56. Such a substrate 54 is made of, for example, glass or polyethylene. The substrate 54 has the same width as the width of the protruding portion 38, and is provided on the protruding portion 38 such that at least a part of the phosphor 56 is located in the urethral catheterization lumen. Specifically, the substrate 54 covers the protruding end surface 38a and the two side surfaces 38b of the protruding portion 38 in a state of being bent in a substantially U-shape. Each end portion of the substrate 54, in an extending direction of the substrate 54, is bent and fitted in a respective one of the latching grooves 41.

The phosphor 56 is made of a material that emits fluorescence when irradiated with the excitation light from the optical fiber 58. Specifically, examples of the material constituting the phosphor 56 include platinum porphyrin, ruthenium complex, pyrene derivative, and the like. The phosphor 56 may be provided with a coating for blocking disturbance light. However, the phosphor 56 may not have such a coating.

The oxygen transmission unit 52 is the optical fiber 58 which is capable of irradiating the phosphor 56 with excitation light and capable of receiving fluorescence from the phosphor 56. The oxygen transmission unit 52 is fixed to the urethral catheter 18 with the position of the distal end surface 58a of the optical fiber 58 fixed with respect to the phosphor 56. The optical fiber 58 may be a glass optical fiber or a plastic optical fiber. The optical fiber 58 may be fixed to the shaft 22 by the fixing portion 60 such that the distal end surface 58a where the core is exposed faces the phosphor 56 at a distance.

The fixing portion 60 includes a fiber support portion 64 that is provided on a wall surface of the urethral catheterization lumen 42 (the wall surface surrounding the urethral catheterization lumen 42) and that has an insertion hole 62 into which a distal portion of the optical fiber 58 is inserted or positioned; and an adhesive 66 for fixing the optical fiber 58 to the wall surface of the urethral catheterization lumen 42. The adhesive 66 seals a through-hole 68 formed on the outer surface of the shaft 22. The adhesive 66 is made of a material that can transmit light from the optical fiber 58 and fluorescence from the phosphor 56. For this reason, even in a case where the adhesive 66 penetrates between the distal end surface 58a of the optical fiber 58, and the substrate 54, the excitation light from the optical fiber 58 is applied to the phosphor 56, and the fluorescence from the phosphor 56 can be received by the optical fiber 58. A position of the distal end surface 58a of the optical fiber 58 in an axial direction of the shaft 22 is substantially the same as the position of the end portion of the urethral catheter port 28 in a distal end direction.

The balloon 24 can be inflated and contracted by changes in internal pressure. That is, the balloon 24 is inflated by the introduction of the inflation fluid into the balloon 24 and is contracted by the inflation fluid being discharged from the balloon 24. FIG. 1 shows the balloon 24 in the inflated state.

The hub 26 is integrally formed in a hollow shape of a resin material or the same material as that of the shaft 22. The hub 26 is provided with a urine port 70 in communication with the urethral catheterization lumen 42 and a balloon inflation port 72 in communication with the inflation lumen 32. The urethral catheterization lumen 42 and the urine port 70 constitute a urine flow lumen 74 as a urine drainage flow path of the urethral catheter 18. A flow rate sensor 76 capable of detecting the flow rate of urine circulating in the urine port 70 is provided on the wall surface of the urine port 70. That is, the flow rate sensor 76 is positioned so that the flow rate sensor 76 contacts the urine circulating in the urine port 70 or in the vicinity of the inside of the wall. The balloon inflation port 72 is configured to be connectable to a pressure application device (not shown) for pumping the inflation fluid into the balloon 24 through the inflation lumen 32. The balloon inflation port 72 also includes a valve structure (not shown) that opens when the pressure application device is connected and closes when it is separated. The hub 26 is configured such that the cable connector 90 of the monitoring system 16 is attachable and detachable.

As shown in FIG. 1, the urine collection bag 14 is configured as a so-called closed bag, and includes a bag main body 78, the urethral catheter tube 80 for guiding urine in the urethral catheter 18 into the bag main body 78, and a urine or discharge portion 82 for discharging urine in the bag main body 78. Such a urine collection bag 14 is integrally formed of a resin material or the like. That is, the bag main body 78, the urethral catheter tube 80 and the discharge portion 82 may be integrally formed as one piece. However, the urine collection bag 14 may be a separate bag.

As shown in FIG. 1 and FIG. 2, the monitoring system 16 includes the cable connector 90 attachable to and detachable from the hub 26, a long transmission cable 92 interlocked to the cable connector 90, and a monitor main body portion 94 interlocked to the transmission cable 92. The cable connector 90 is provided with an oxygen cable 96 optically connected to the oxygen transmission unit 52; a temperature cable 98 electrically connected to the temperature transmission unit 48; and a flow rate cable 100 electrically connected to the flow rate sensor 76. The oxygen cable 96 is an optical fiber, and the temperature cable 98 and the flow rate cable 100 are electric wires. The oxygen cable 96, the temperature cable 98, and the flow rate cable 100 are bundled together by the transmission cable 92 and extend to the monitor main body portion 94.

The transmission cable 92 is disposed along the urethral catheter tube 80, and is locked to or fixed with respect to the urethral catheter tube 80 by a plurality of latch sections 102 (banding bands). Accordingly, hindrance of the oxygen measurement device 10A by the urethral catheter tube 80 and the transmission cable 92 can be suppressed.

Figure 6:
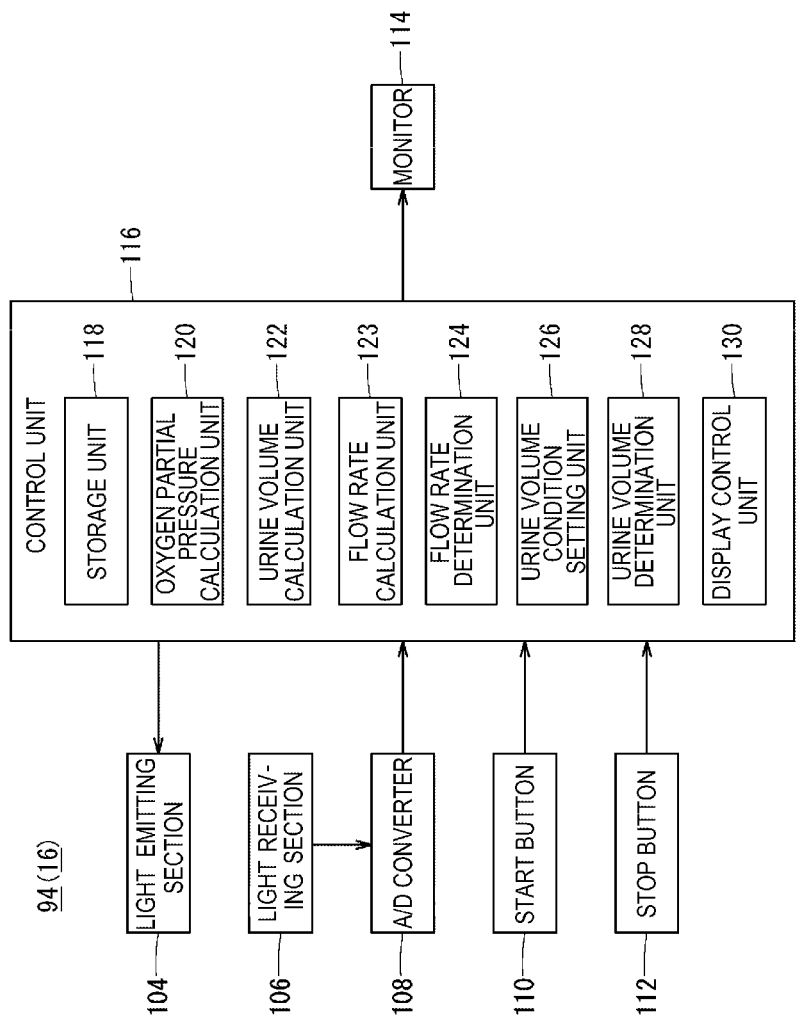
FIG. 6 is a block diagram illustrating a monitor main body portion shown in FIG. 1.

As shown in FIG. 6, the monitor main body portion 94 includes a light emitting section 104, a light receiving section 106, an A/D converter 108, a start button 110, a stop button 112, a monitor 114, and a control unit 116.

The light emitting section 104 is, for example, a light emitting diode, and emits excitation light of a predetermined wavelength to the oxygen cable 96. The light receiving section 106 is, for example, a photodiode, and the fluorescence transmitted from the oxygen cable 96 is incident. The A/D converter 108 converts the light reception signal of the light receiving section 106 into a digital value and outputs the digital value to the control unit 116.

The start button 110 is a button for starting measurement of an oxygen partial pressure in urine. The stop button 112 is a button for stopping measurement of the oxygen partial pressure in urine. The monitor main body portion 94 is also provided with a power button (not shown) and the like.

The monitor 114 is configured to be able to display the oxygen partial pressure in urine calculated by the control unit 116. The monitor 114 is a so-called full dot liquid crystal type display, and can display predetermined information in color. The monitor 114 has a touch panel function, and also functions as an input unit for inputting predetermined information. As an input format by the monitor 114, a pointing device such as a mouse cursor type, a touch pen type, and a touch pad type can be used in addition to the touch panel type. The input of information to the monitor main body portion 94 is not limited to the input by the monitor 114, and may be input by an input button or the like.

The control unit 116 includes a storage unit 118 and various function implementation units. The function implementation unit is a software function unit whose function is realized by the central processing unit (CPU) executing a program stored in the storage unit 118; however, it can be realized by a hardware functional unit formed of an integrated circuit such as a Field-Programmable Gate Array (FPGA). The storage unit 118 includes a writable non-volatile memory (for example, a flash memory), and can store information input via the monitor 114, information calculated by the control unit 116, and the like.

The control unit 116 includes a storage unit 118, an oxygen partial pressure calculation unit 120, a urine volume calculation unit 122, a flow rate calculation unit 123, a flow rate determination unit 124, a urine volume condition setting unit 126, a urine volume determination unit 128, and a display control unit 130. The control unit 116 further includes a temperature input unit (not shown) to which the output signal of the temperature sensor 44 is input, and a flow rate input unit (not shown) to which the output signal of the flow rate sensor 76 is input.

The oxygen partial pressure calculation unit 120 calculates the oxygen partial pressure in urine based on the output signal of the oxygen sensor 20 and the output signal of the temperature sensor 44. The urine volume calculation unit 122 calculates an amount of urine based on the output signal of the flow rate sensor 76. The flow rate calculation unit 123 calculates the flow rate V of the urine in the urine flow lumen 74 based on the output signal from the flow rate sensor 76.

The urine volume condition setting unit 126 sets a predetermined urine volume condition. Specifically, the urine volume condition setting unit 126 sets the first urine volume determination value and the second urine volume determination value. The first urine volume determination value is calculated by multiplying, for example, a first urine volume reference value (0.5 ml/kg/h) used for determination of the first stage and second stage of acute kidney injury (AKI) by the weight of the patient. The second urine volume determination value is calculated by multiplying a second urine volume reference value (0.3 ml/kg/h) used for determination of the third stage of acute kidney injury by the weight of the patient. However, the urine volume condition setting unit 126 can set any condition. The urine volume determination unit 128 determines whether or not the urine volume calculated by the urine volume calculation unit 122 matches a predetermined urine volume condition.

The display control unit 130 changes the format of display of the oxygen partial pressure on the monitor 114 according to the flow rate V of urine acquired based on the output signal of the flow rate sensor 76. Specifically, the display control unit 130 causes the monitor 114 to display the oxygen partial pressure in the first display format when the flow rate determination unit 124 determines that the flow rate V of urine is equal to or higher than a predetermined value (equal to or higher than a reference flow rate V0), and causes the monitor 114 to display the oxygen partial pressure in a second display format different from the first display format when the flow rate determination unit 124 determines that the flow rate V of urine is less than a predetermined value (less than a reference flow rate V0). The display control unit 130 causes the monitor 114 to display a graph indicating temporal changes in oxygen partial pressure.

When the urine volume determination unit 128 determines that the urine volume corresponds to the urine volume condition, the display control unit 130 causes the monitor 114 to display a message indicating the result.

Next, assembly of the oxygen sensor 20 to the urethral catheter 18 will be described. In the present embodiment, the optical fiber 58 is disposed in the urethral catheterization lumen 42, and the distal end of the optical fiber 58 is inserted into the insertion hole 62 of the fiber support portion 64. Then, the optical fiber 58 is fixed to the shaft 22 by injecting the adhesive 66 from the outside of the shaft 22 through the through-hole 68. In addition, in a state where the substrate 54 of the oxygen sensor main body 50 is bent in a U-shape, the end portions of the substrate 54 are each locked in a respective one of the latching grooves 41 of the protruding portion 38. Furthermore, with the adhesive 66 applied to the distal end surface of the shaft 22 and the wall surface of the distal end opening portion 34, the closing portion 23 holding the oxygen sensor main body 50 is fitted to the distal end opening portion 34 of the shaft 22. Then, the closing portion 23 is fixed to the shaft 22, and the oxygen sensor main body 50 is fixed to the shaft 22. Accordingly, the phosphor 56 and the distal end surface 58a of the optical fiber 58 can be positioned with high accuracy.

A use of the oxygen measurement device 10A will now be described.

Figure 7:
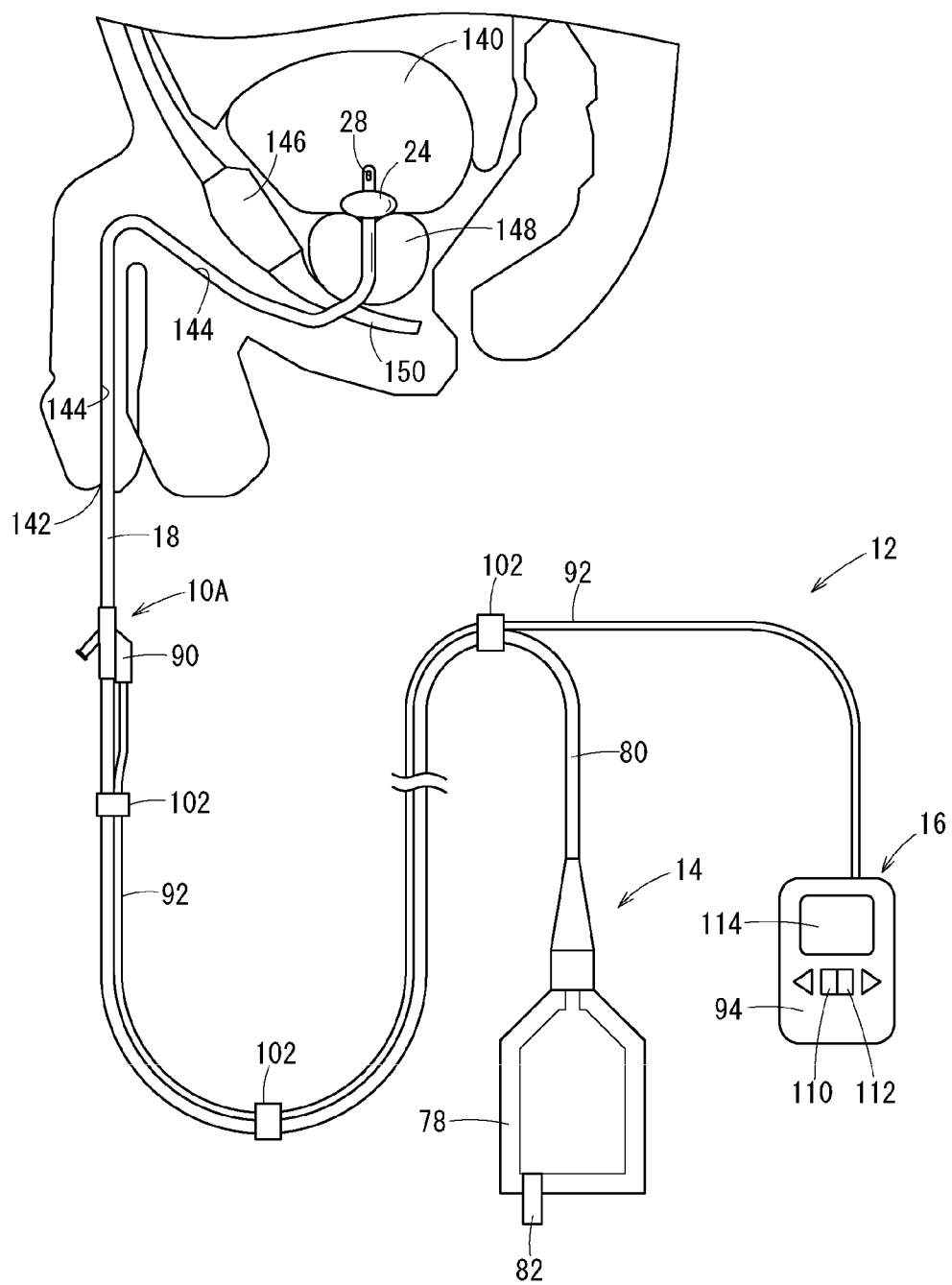
FIG. 7 is a schematic view illustrating a method for using the oxygen measurement system.
Figure 8:
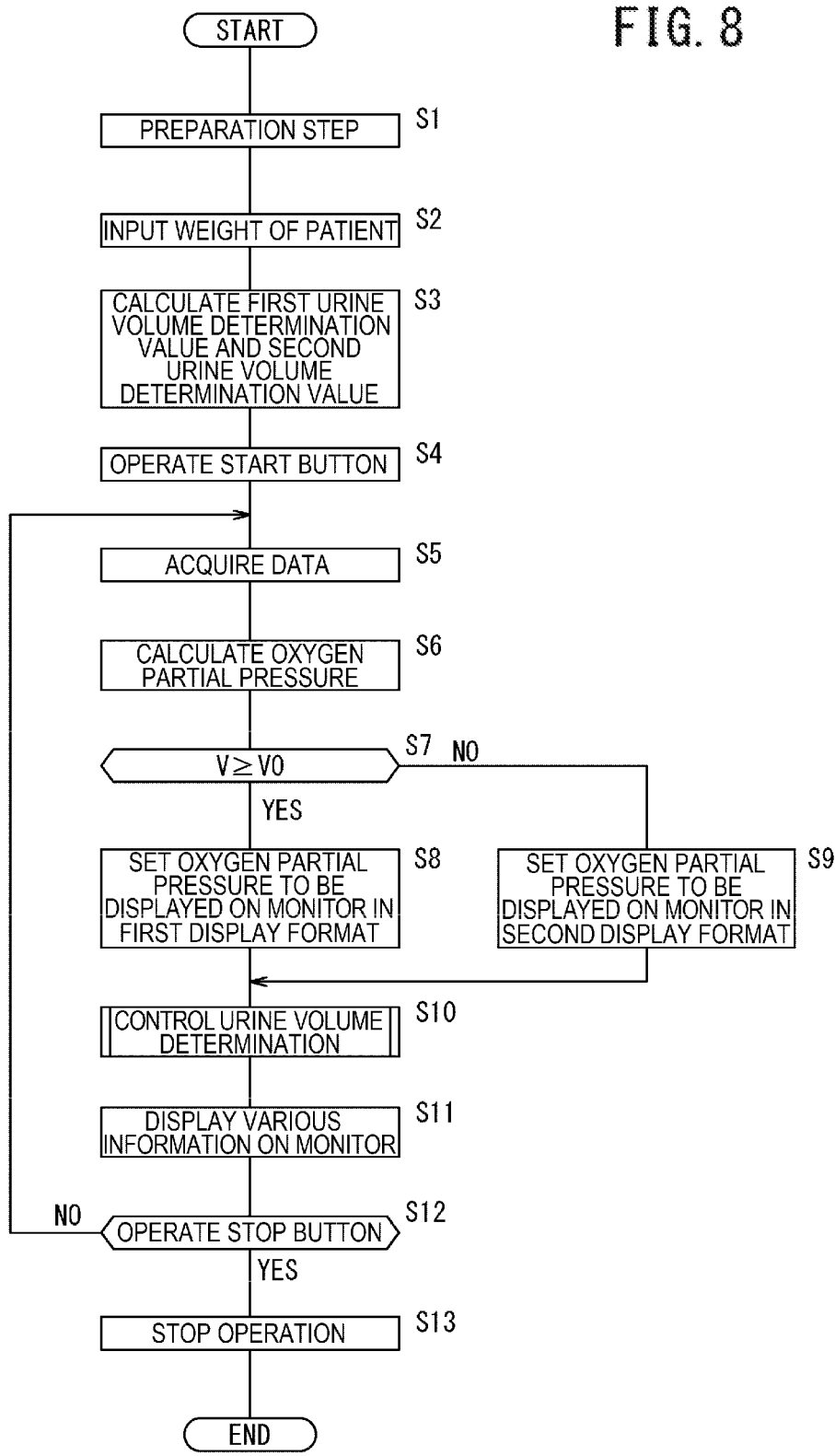
FIG. 8 is a first flow chart illustrating the method for using the oxygen measurement system.

As shown in FIGS. 7 and 8, first, the preparation process is performed (step S1 in FIG. 8). In the preparation step, the tip or distal portion of the urethral catheter 18 is indwelled in the bladder 140. Specifically, the distal end of the shaft 22 coated with lubricating jelly is inserted into the urethra 144 from the urethral orifice 142 of the patient, and the distal end of the shaft 22 is advanced to position the urethral catheter port 28 and the balloon 24 in the bladder 140. The urethral catheter 18 may be easily inserted into the bladder 140 by inserting a stylet (not shown) into the urethral catheterization lumen 42 in the shaft 22 to impart sufficient rigidity to the shaft 22.

Thereafter, the balloon 24 is inflated by pumping the inflation fluid from a pressure application device (not shown) from the inflation port to the inflation lumen 32 (refer to FIG. 2). Accordingly, the urethral catheter 18 is prevented from coming out of the body, and a distal portion of the shaft 22 that is distal of the balloon 24 is indwelled in the bladder 140. Reference numeral 146 in FIG. 7 is a pubic bone, reference numeral 148 is a prostate, and reference numeral 150 is an external urinary sphincter.

When the distal portion of the urethral catheter 18 is indwelled in the bladder 140, the urine in the bladder 140 can be excreted via the urethral catheter 18 into the urine collection bag 14. At this time, in the urethral catheter 18, urine in the bladder 140 flows into the urine flow lumen 74 by way of the urethral catheter port 28.

In addition, the user inputs the weight of the patient into the monitor main body portion 94 (step S2). Then, the urine volume condition setting unit 126 calculates the first urine volume determination value and the second urine volume determination value based on the input patient weight (step S3).

Thereafter, the user operates the start button 110 (step S4). Accordingly, measurement of the oxygen partial pressure in urine is started. When the start button 110 is operated, measurement of the oxygen partial pressure in urine is performed continuously or intermittently (for example, every 5 minutes) until the stop button 112 is operated.

Specifically, the control unit 116 acquires various data (step S5). In other words, the control unit 116 acquires the output signal of the temperature sensor 44 and the output signal of the flow rate sensor 76. Furthermore, the control unit 116 controls the light emitting section 104 to emit excitation light of a predetermined wavelength. Then, the excitation light emitted from the light emitting section 104 is transmitted to the optical fiber 58 through the oxygen cable 96, and the phosphor 56 of the oxygen sensor main body 50 is irradiated therewith from the distal end surface 58a of the optical fiber 58. The phosphor 56 irradiated with excitation light transitions from the ground state to the excited state, and returns to the ground state while emitting fluorescence. At this time, when oxygen molecules exist around the phosphor 56, the interaction deprives the excitation energy to oxygen molecules, and the intensity of fluorescence emission decreases. This phenomenon is called a quenching phenomenon, and the intensity of fluorescence emission is inversely proportional to an oxygen molecule concentration. The fluorescence of the phosphor 56 is incident from the distal end surface 58a of the optical fiber 58 and is guided to the light receiving section 106 through the optical fiber 58 and the cable 96 for oxygen. The light reception signal of the light receiving section 106 is converted into a digital signal by the A/D converter 108 and input to the control unit 116. Accordingly, the output signal of the oxygen sensor 20 is acquired.

Thereafter, the oxygen partial pressure calculation unit 120 calculates the oxygen partial pressure in urine based on the output signal of the oxygen sensor 20 (the output signal of the A/D converter 108) and the output signal of the temperature sensor 44 (step S6). In addition, the flow rate determination unit 124 determines whether or not the flow rate V of urine acquired is equal to or higher than a predetermined value (reference flow rate V0) based on the output signal of the flow rate sensor 76 (step S7). The reference flow rate V0 is stored in advance in the storage unit 118.

When the flow rate determination unit 124 determines that the flow rate V is equal to or higher than the reference flow rate V0 (step S7: YES), the display control unit 130 performs setting so that the calculated oxygen partial pressure is displayed on the monitor 114 in the first display format (step S8). On the other hand, when the flow rate determination unit 124 determines that the flow rate V is less than the reference flow rate V0 (step S7: NO), the display control unit 130 performs setting so that the calculated oxygen partial pressure is displayed on the monitor 114 in the second display format (step S9).

Figure 9:
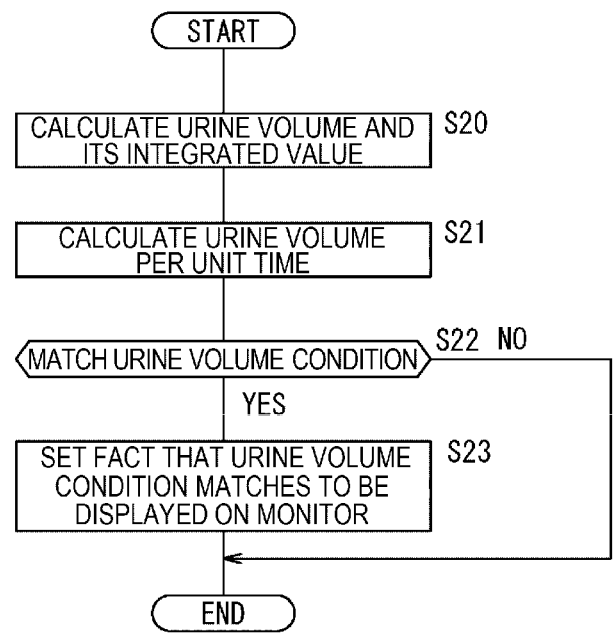
FIG. 9 is a second flow chart illustrating the method for using the oxygen measurement system.

Subsequently, urine volume determination control (step S10) is performed. In the urine volume determination control (step S10), the urine volume calculation unit 122 first calculates the urine volume and its integrated value (step S20 in FIG. 9). In other words, the urine volume calculation unit 122 calculates an amount of urine based on the output signal of the flow rate sensor 76. The calculated urine volume is stored in the storage unit 118. Then, the urine volume calculation unit 122 calculates the integrated value of the urine volume by adding the urine volume calculated in the present measurement to the urine volume stored in the storage unit 118. The integrated value of the urine volume is stored in the storage unit 118.

Thereafter, the urine volume calculation unit 122 calculates the urine volume per unit time (for example, per hour) based on the integrated value of the urine volume (step S21). Subsequently, the urine volume determination unit 128 determines whether or not the urine volume per unit time matches the urine volume condition (step S22).

Specifically, the urine volume determination unit 128 determines whether or not the urine volume per unit time corresponds to any one of the first to third stages of AKI. More specifically, the urine volume determination unit 128 determines that the urine volume per unit time corresponds to the first stage when the urine volume per unit time remains less than the first urine volume determination value for six hours or more. In addition, the urine volume determination unit 128 determines that the urine volume per unit time corresponds to the second stage when the urine volume per unit time remains less than the first urine volume determination value for 12 hours or more. Furthermore, the urine volume determination unit 128 determines that the urine volume per unit time corresponds to the third stage when the urine volume per unit time remains less than the second urine volume determination value for 24 hours or more or when no urine volume remains for 12 hours or more.

When the urine volume determination unit 128 determines that the urine volume per unit time corresponds to any one of the first to third stages of AKI (step S22: YES), the display control unit 130 causes the monitor 114 to display a message indicating that the urine volume per unit time corresponds to the urine volume condition (any one of the first to third stages) (step S23), and causes the process to proceed to the step S11 in FIG. 8. On the other hand, when the urine volume determination unit 128 determines that the urine volume per unit time does not correspond to any of the first to third stages of AKI (step S22: NO), the display control unit 130 causes the process to proceed to the step S11 in FIG. 8.

Figure 10:
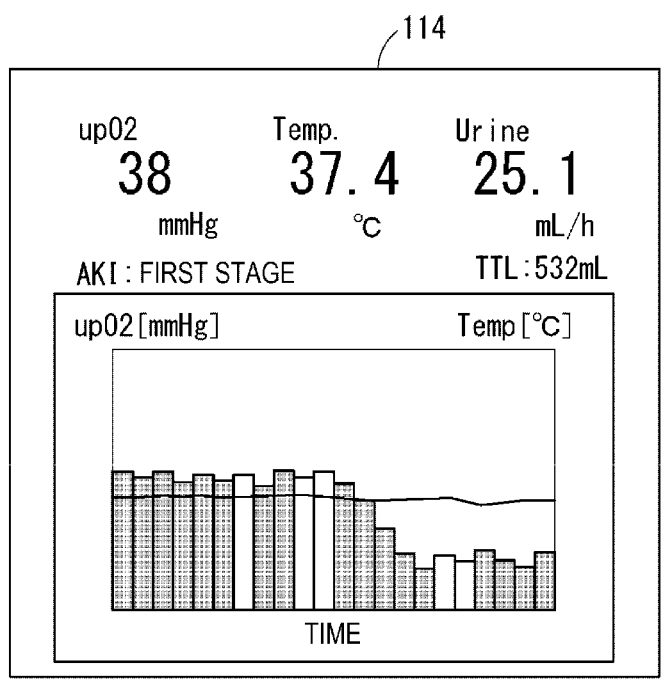
FIG. 10 is a first view showing measurement results of the oxygen measurement system which are displayed on a monitor.

Thereafter, in step S11, the display control unit 130 causes the monitor 114 to display various pieces of information. Specifically, as shown in FIG. 10, the display control unit 130 causes the monitor 114 to numerically display, for example, the oxygen partial pressure, the temperature in the bladder 140, the urine volume, and the integrated value of the urine volume, and causes the monitor 114 to display temporal changes in oxygen partial pressure and temporal changes in the temperature in the bladder 140 in the form of a graph. In addition, when the urine volume determination control determines that the urine volume per unit time corresponds to any one of the first to third stages of AKI (step S22: YES), the display control unit 130 causes the monitor 114 to display a message indicating the result. The display control unit 130 does not cause the monitor 114 to display the AKI when the urine volume determination control determines that the urine volume per unit time does not correspond to any of the first to third stages of AKI (step S22: NO).

In the example of FIG. 10, the oxygen partial pressure of 38 mmHg, the temperature in the bladder 140 of 37.4° C., the urine volume per unit time of 25.1 mL/h, the cumulative volume of urine of 532 mL, and AKI being the first stage are displayed. In addition, the temporal changes in oxygen partial pressure are displayed in the form of a bar graph, and the temporal changes in the temperature in the bladder 140 are displayed in the form of a line graph. That is, the horizontal axis represents time, one vertical axis represents oxygen partial pressure (mmHg), and the other vertical axis represents temperature (° C.). Furthermore, in the bar graph, the filled portion is a portion displaying the oxygen partial pressure in the first display format, and the non-filled portion is a portion displaying the oxygen partial pressure in the second display format. As shown in FIG. 10, the first display format and the second display format are visually distinguishable formats. In other words, in the bar graph, the oxygen partial pressure in the filled portion is the oxygen partial pressure in urine when the flow rate V of urine is equal to or higher than the reference flow rate V0, the oxygen partial pressure in the unfilled part is the oxygen partial pressure in urine when the flow rate V of urine is less than the reference flow rate V0.

The first display format and the second display format of the oxygen partial pressure are not limited to the example of FIG. 10. For example, in the bar graph, the first display format may be displayed in a non-filled state, and the second display format may be displayed in a filled state.

Figure 11A:
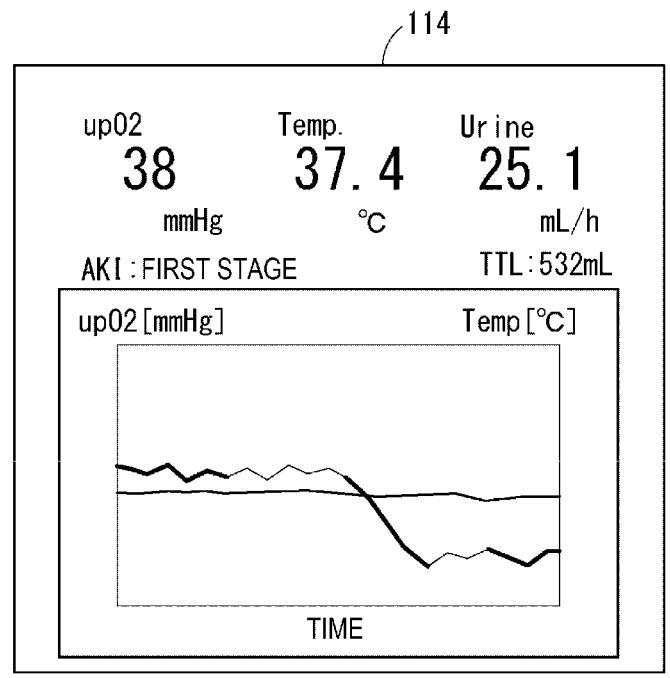
FIG. 11A is a second view showing measurement results of the oxygen measurement system which are displayed on the monitor.

In addition, as shown in FIG. 11A, the display control unit 130 may cause the monitor 114 to display a temporal change in oxygen partial pressure as a line graph. In this case, in the line graph, a thick line portion indicates the oxygen partial pressure in the first display format, and a thin line portion indicates the oxygen partial pressure in the second display format. However, this can be varied, for example the first display format may be displayed as a thin line, and the second display format may be displayed as a thick line.

Figure 11B:
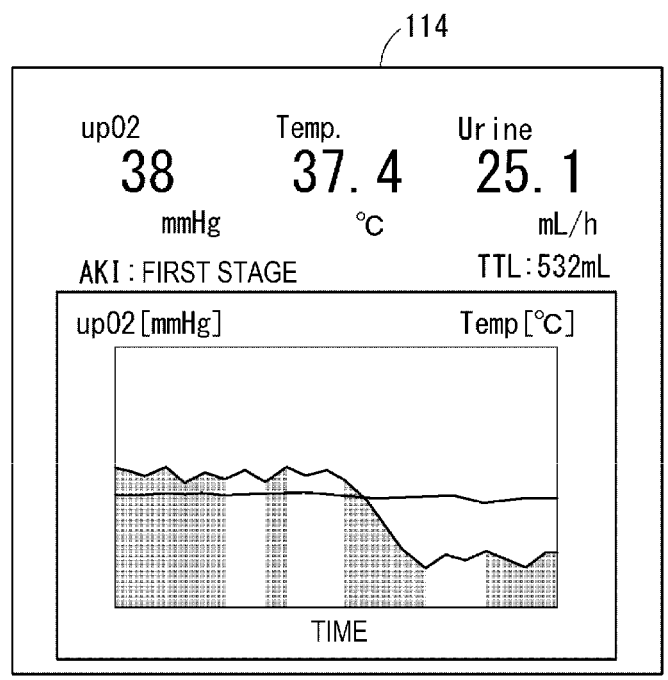
FIG. 11B is a third view showing measurement results of the oxygen measurement system which are displayed on the monitor.

In addition, as shown in FIG. 11B, in the line graph, a portion in which the lower side of the line segment indicating the value of the oxygen partial pressure is filled may be taken as the first display format of the oxygen partial pressure, and a portion in which the lower side is not filled up may be taken as the second display format of the oxygen partial pressure. However, the first display format may be displayed in a state in which the lower side is a not filled, and the second display format may be displayed in a state in which the lower side is a filled.

Thereafter, the control unit 116 determines whether or not the stop button 112 is operated (step S12). In a case where the stop button 112 has not been operated (step S12: NO), the processes after step S5 are performed. On the other hand, in a case where the stop button 112 is operated (step S12: YES), the control unit 116 stops the operation of the oxygen measurement. In other words, the light emission of excitation light of the light emitting section 104 is stopped. At this stage, the oxygen measurement process of the present flowchart ends.

Next, effects of the present embodiment will be described.

The monitoring system 16 is connected to the oxygen measurement device 10A capable of detecting an oxygen partial pressure of urine and flow of urine in the urine flow lumen 74 of the urethral catheter 18. The monitoring system 16 includes an oxygen partial pressure calculation unit 120 that calculates an oxygen partial pressure in urine based on an output signal from the oxygen measurement device 10A (oxygen sensor 20); a monitor 114 that displays the oxygen partial pressure calculated by the oxygen partial pressure calculation unit 120; and a display control unit 130 that changes the format of display of the oxygen partial pressure on the monitor 114 according to the flow rate V of urine acquired based on the output signal from the oxygen measurement device 10A (flow rate sensor 76).

Accordingly, by looking at the format of display of the oxygen partial pressure on the monitor 114, it is possible to easily confirm whether or not a measured oxygen partial pressure is an oxygen partial pressure which is in urine flowing stably and which appropriately reflects a state of the kidneys.

The monitoring system 16 includes a flow rate determination unit 124 that determines whether or not the flow rate V of urine acquired is equal to or higher than a predetermined value (equal to or higher than a reference flow rate V0). The display control unit 130 displays the oxygen partial pressure on the monitor 114 in the first display format in a case where the flow rate determination unit 124 determines that the flow rate V of urine is equal to or higher than a predetermined value, and displays the oxygen partial pressure on the monitor 114 in a second display format different from the first display format in a case where the flow rate determination unit 124 determines that the flow rate V of urine is less than a predetermined value. Accordingly, in a case where the monitor 114 displays the oxygen partial pressure in the first display format, it is possible to easily confirm that the measured oxygen partial pressure is an oxygen partial pressure in urine flowing at a flow rate equal to or higher than a reference flow rate V0. In addition, in a case where the monitor 114 displays the oxygen partial pressure in the second display format, it is possible to easily confirm that the measured oxygen partial pressure is an oxygen partial pressure in urine at a flow rate less than a reference flow rate V0. Accordingly, it is possible to easily confirm whether or not the oxygen partial pressure is an oxygen partial pressure which is acquired in a state that appropriately reflects a state of the kidneys.

The display control unit 130 causes the monitor 114 to display a graph indicating temporal change in oxygen partial pressure. For this reason, it is possible to more easily confirm whether or not the measured oxygen partial pressure is an oxygen partial pressure in urine flowing at a flow rate equal to or higher than a predetermined value. Accordingly, it is possible to easily confirm whether a state of the kidneys is in better state as compared to the previous state, and it is possible to perform interventions such as treatment and its adjustment at appropriate timing as needed.

The oxygen partial pressure calculation unit 120 calculates the oxygen partial pressure in urine corrected by a temperature in the urine acquired based on the output signal from the oxygen measurement device 10A (temperature sensor 44). Accordingly, it is possible to display a more accurate oxygen partial pressure in urine which has been temperature-corrected on the monitor 114.

The monitoring system 16 includes a urine volume calculation unit 122 that calculates a urine volume circulating in the urine flow lumen based on the output signal from the oxygen measurement device 10A (flow rate sensor 76); and a urine volume determination unit 128 that determines whether or not the urine volume calculated by the urine volume calculation unit 122 matches a predetermined urine volume condition. When the urine volume determination unit 128 determines that the urine volume corresponds to the urine volume condition, the display control unit 130 causes the monitor 114 to display a message indicating the result. Accordingly, it is possible to easily confirm whether or not the urine volume matches a predetermined urine volume condition (for example, whether or not the urine volume is excessively small). Therefore, it is possible to easily confirm whether a state of the kidneys is in better state as compared to the previous state, and it is possible to perform interventions such as treatment and its adjustment at appropriate timing as needed.

In the monitoring system 16, the display control unit 130 may be configured to display the oxygen partial pressure on the monitor 114 in a case where the flow rate determination unit 124 determines that the flow rate V of urine is equal to or higher than a predetermined value, and not to display the oxygen partial pressure on the monitor 114 in a case where the flow rate determination unit 124 determines that the flow rate V of urine is less than a predetermined value. Accordingly, in a case where the monitor 114 displays the oxygen partial pressure, it is possible to easily confirm that the measured oxygen partial pressure is an oxygen partial pressure in urine flowing at a flow rate equal to or higher than a predetermined value. Accordingly, it is possible to easily confirm or identify whether or not the oxygen partial pressure is an oxygen partial pressure which is acquired in a state that appropriately reflects a state of the kidneys.

The monitoring system 16 may be connectable to the oxygen measurement device 10A capable of detecting an oxygen partial pressure of urine and flow of urine in the bladder 140 and flowing outside the urethral catheter 18.

Next, an oxygen measurement device 10B according to a modification example will be described. In the oxygen measurement device 10B according to the modification example, the features or components that are the same as those of the above-described oxygen measurement device 10A are denoted by the same reference numerals, and a detailed description of such features or components is not repeated.

Figure 12:
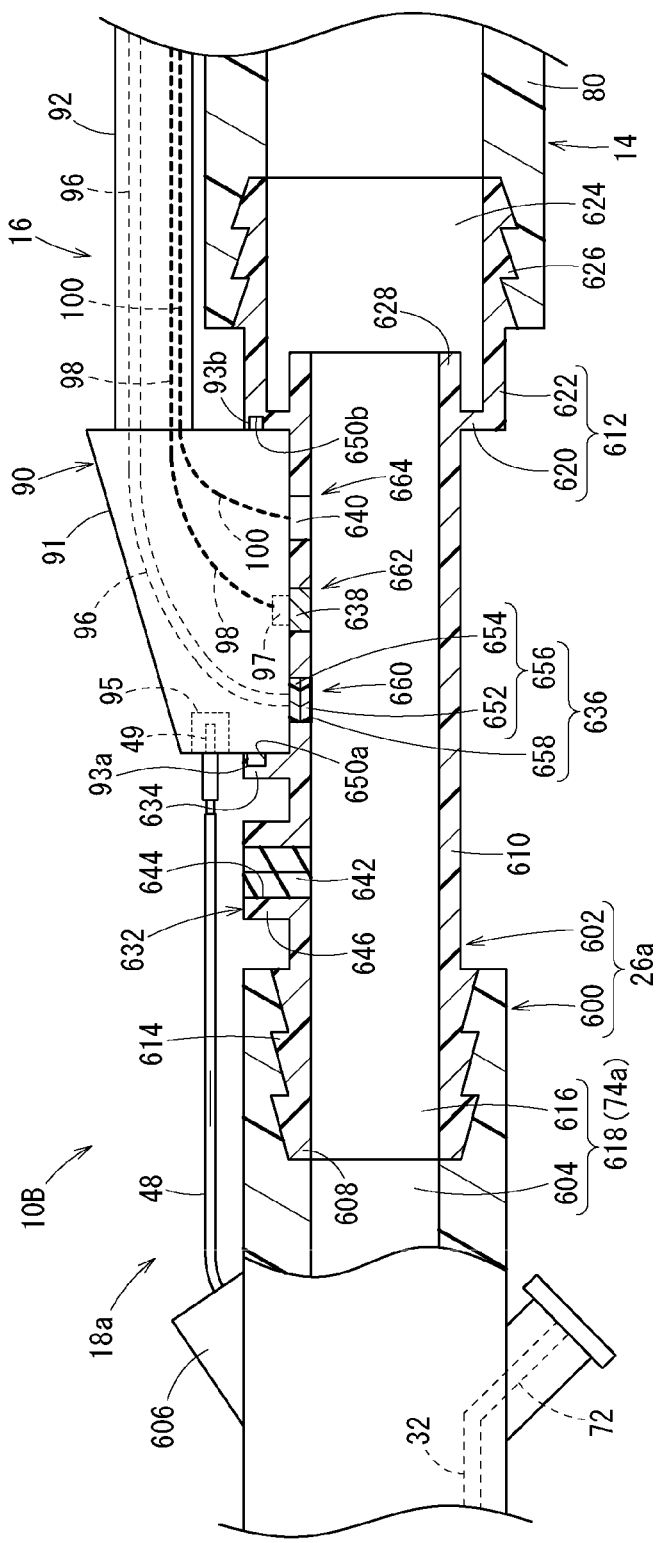
FIG. 12 is a cross-sectional view showing a modification example of an oxygen measurement device.

As shown in FIG. 12, the urethral catheter 18a of the oxygen measurement device 10B according to the modification example includes a hub 26a. The hub 26a comprises a hollow hub main body 600 provided at the proximal end of the shaft 22, and a hollow interlock portion 602 provided at the proximal end of the hub main body 600. The hub main body 600 is integrally formed (monolithic structure) of resin material. In FIG. 12, the hub main body 600 has a first urine lumen 604 in communication with the urethral catheterization lumen 42, a balloon inflation port 72 in communication with the inflation lumen 32, and a lead-out port 606 for leading out the proximal portion of the temperature transmission unit 48 to the outside. The balloon inflation port 72 is configured to be connectable to a pressure application device (not shown) for pumping the inflation fluid into the balloon 24 through the inflation lumen 32.

The interlock portion 602 is integrally formed (monolithic structure) in a tubular shape by a resin material having transparency (transparent resin material). The interlock portion 602 includes a first connection section 608 fitted into the proximal end opening portion of the hub main body 600, an interlock portion main body 610 provided at the proximal end of the first connection section 608, and a second connection section 612 provided at the proximal portion of the interlock portion main body 610 and fitted into the distal end opening portion of a urethral catheter tube 80 of the urine collection bag 14. As shown in FIG. 12, the first connection section 608 is at the distal end of the interlock portion 602, and the second connection section 612 is at the proximal end of the interlock portion 602.

The outer surface of the first connection section 608 is in fluid tight contact with the inner surface of the proximal end opening portion of the hub main body 600 by providing a plurality of annular protrusion portions 614 on the outer surface of the first connection section 608 in the axial direction that engage similarly configured portions on the inner surface of the proximal end opening portion of the hub main body 600. A second urine lumen 616 communicating with the first urine lumen 604 is formed in the first connection section 608 and the interlock portion main body 610. Hereinafter, the first urine lumen 604 and the second urine lumen 616 may be collectively referred to as a urine lumen 618. The urine port 618 constitutes the urine flow lumen 74a of the urethral catheter 18a. The cross-sectional shapes of the urethral catheterization lumen 42 and the urine lumen 618 may be formed identical (for example, rectangular) to each other. That is, the flow path cross-sectional areas of the urethral catheterization lumen 42 and the urine lumen 618 may be identical to each other. Accordingly, it is possible to suppress the occurrence of disturbance in the urine flowing from the urethral catheterization lumen 42 to the urine lumen 618, and therefore it is possible to circulate the urine smoothly.

The second connection section 612 includes an annular protruding portion 620 protruding outward (radially outward) from the interlock portion 602 and an extension portion 622 extending in the proximal (axial) direction from the annular protruding portion 620. The flow path cross-sectional area of the lumen 624 of the second connection section 612 is larger than the flow path cross-sectional area of the second urine lumen 616. A plurality of annular protrusion portions 626 are provided in the axial direction on the outer surface of the extension portion 622 so that the outer surface of the extension portion 622 is in fluid tight contact with the inner surface of the distal end opening portion of the urethral catheter tube 80. The proximal portion of the interlock portion main body 610 protrudes into the lumen 624 of the second connection section 612. The flow path cross-sectional area of the proximal side opening portion of the protruding portion 628 (inflow suppressing portion) which protrudes into the lumen 624 of the second connection section 612 in the interlock portion main body 610 is smaller than flow path cross-sectional area of the lumen 624 of the second connection section 612. That is, because of surface tension, the urine can come into contact with the wall surface constituting the proximal end opening portion of the protruding portion 628, so that air can be prevented from flowing from the lumen 624 of the second connection section 612 while urine can be prevented from flowing into the second urine lumen 616.

In the interlock portion main body 610, a port portion 632 for introducing a predetermined fluid into the second urine lumen 616, a support wall portion 634 located on the proximal side of the port portion 632, an oxygen sensor main body 636 constituting the oxygen sensor 660 for detecting oxygen in urine in the second urine lumen 616, a temperature sensor main body 638 constituting the temperature sensor 662 for detecting the temperature of urine in the second urine lumen 616, and a flow rate sensor main body 640 constituting the flow rate sensor 664 for detecting the flow rate of urine in the second urine lumen 616 are provided.

The port portion 632 is distal of the oxygen sensor main body or sensor for detecting oxygen in urine 636, and includes a valve body support portion 646 having a hole 644 in which a valve body 642 is disposed. The valve body 642 is formed of an elastic member 654 such as rubber, and for example, a hollow needle body of the syringe (not shown) is configured to be able to puncture in a fluid tight manner. The port portion 632 may function as a urine collection port portion for collecting urine in the second urine lumen 616.

Fixing holes 650a and 650b for fixing a cable connector 90 of the monitoring system 16 are formed in each of a surface of the support wall portion 634 that faces the proximal direction and a surface facing the tip (distal) direction of the annular protruding portion 620. The oxygen sensor main body 636, the temperature sensor main body 638, and the flow rate sensor main body 640 are arranged in a row in this order from the distal side between the support wall portion 634 and the protruding portion 628 in a mutually separated manner. That is, the sensor that detects oxygen in urine 636, the sensor that detects urine temperature 638 and the sensor that detects urine flow rate 640 are arranged axially one after another in an axially spaced apart manner, with the sensor that detects urine temperature 638 being positioned axially between the sensor that detects oxygen in urine 636 and the sensor that detects urine flow rate 640, whereby the sensor that detects oxygen in urine 636 is distal of the sensor that detects urine temperature 638, and the sensor that detects urine flow rate 640 is proximal of the sensor that detects urine temperature 638 as shown in FIG. 12.

The oxygen sensor main body 636 is proximal of the port portion 632 and distal of the temperature sensor main body 638 and the flow rate sensor main body 640, and has a base part 656 having a substrate 652 and an elastic portion 654, and a phosphor 658 provided on the base part or support 656. The phosphor 658 is applied to the surface of the substrate 652 so as to contact the urine in the second urine lumen 616. The elastic portion 654 is provided on the back surface of the substrate 652 opposite to the phosphor 658. Each of the substrate 652 and the elastic portion 654 is made of a transparent material. The substrate 652 and the phosphor 658 are configured in the same manner as the substrate 54 and the phosphor 56 described above. The elastic portion 654 is made of a flexible resin material such as rubber. The phosphor 658 has a larger area than the distal end surface of the oxygen cable 96 to be described later.

The temperature sensor main body 638 is proximal of the oxygen sensor main body 636 and distal of the flow rate sensor main body 640. In other words, the temperature sensor main body 638 is located near the oxygen sensor main body 636. The temperature sensor main body 638 is configured as a metal plate. The metal plate is preferably made of, for example, a material having a high thermal conductivity such as silver, copper, gold, stainless steel, or aluminum. In this case, a temperature of the temperature sensor main body 638 can be made substantially the same as a temperature of the urine in the second urine lumen 616. However, when the temperature sensor main body 638 can approximate a temperature of the temperature sensor main body 638 to a temperature of urine in the second urine lumen 616, the temperature sensor main body 638 may be a thin plate made from a material other than metal such as resin material. The flow rate sensor main body 640 is proximal of the temperature sensor main body 638, and is configured as, for example, a Karman vortex type or thermal flow rate sensor 664.

The cable connector 90 includes a housing 91, and in the housing 91, the oxygen cable 96 as an optical fiber optically connectable to the oxygen sensor main body 636, a temperature detection unit 97 which can contact or approach the temperature sensor main body 638, a temperature cable 98 electrically connectable to the temperature detection unit 97, and a flow rate cable 100 electrically connectable to flow rate sensor main body 640 are provided.

The cable connector 90 is attachable to and detachable from the hub 26a in a direction intersecting (orthogonal to) the axis of the hub 26a. The housing 91 is provided with a pin 93a that can be inserted into the fixing hole 650a and a pin 93b that can be inserted into the fixing hole 650b. By operating an operation portion (not shown) provided on the housing 91, each of the pins 93a and 93b is configured to be displaceable at a lock position which protrudes outward of the housing 91 and can be inserted into each of fixing holes 650a and 650b, and a withdrawing position retracted inside the housing 91 and withdrawn from the fixing holes 650a and 650b. The housing 91 is provided with a connection terminal 95 to which the terminal 49 provided at the proximal end of the temperature transmission unit 48 can be electrically connected. A cable (not shown) is electrically connected to the connection terminal 95.

The control unit 116 further includes a temperature input unit (not shown) to which the output signal of the temperature sensor 662 is input, and a flow rate input unit (not shown) to which the output signal of the flow rate sensor 664 is input.

In the case of this oxygen measurement device 10B according to the modification example, the same effects as in the case of the oxygen measurement device 10A described above can be acquired.

The oxygen measurement devices 10A and 10B may include a pressure sensor that measures the pressure near the distal end of the urethral catheter 18, 18a. The pressure sensor outputs an electrical or optical signal to the monitoring system 16.

The monitor main body portion 94 may be configured to be able to acquire time, atmospheric pressure around the monitor main body portion 94, humidity around the monitor main body portion 94, and temperature around the monitor main body portion 94. The time includes the current time and an elapsed time from a certain timing. The monitor main body portion 94 can be configured to be able to read and reflect a calibration value at a unique initial period (at the time of manufacture) of each sensor. Regarding a method of inputting the calibration value, it may be input by scanning a one-dimensional or two-dimensional barcode or may be input directly from the monitor 114. Alternatively, the calibration value may be held at a signal output unit of the urethral catheter 18 or 18a and automatically read by connecting the monitoring system 16 to the urethral catheter 18 or 18a.

In the oxygen measurement system 12, operation confirmation may be performed before use. In this case, it is confirmed that an output value from each sensor of the oxygen measurement device 10A or 10B is within the normal operation range. Specifically, a reference value calculated from the temperature, humidity, and atmospheric pressure around the monitor main body portion 94 is compared with an output value from each sensor of the oxygen measurement device 10A or 10B. Then, the control unit 116 of the monitor main body portion 94 determines whether or not the output value from each sensor of the oxygen measurement device 10A or 10B is within the normal range, and reports the determination results. In addition, whether or not the output value from each sensor of the oxygen measurement device 10A or 10B is within the normal range may be confirmed by acquiring the output value of each sensor using a reference solution or reference gas, and comparing the output value with the reference value.

The monitor main body portion 94 may notify various physical quantities (oxygen partial pressure, temperature in the bladder 140, urine volume, and the like) based on the output values from the sensors of the oxygen measurement device 10A or 10B. Specifically, the monitor main body portion 94 can notify the physical quantity by a numerical value, bar graph, dial gauge, level meter, color or the like. In addition, the monitor main body portion 94 can display the transition of the physical quantity on the monitor 114 by the up and down arrows, various graphs (such as line graphs), color change progress display, and the like.

There is a time lag before changes in the bladder 140 appear as changes in urine flow rate in the oxygen measurement device 10A or 10B. For this reason, the monitor main body portion 94 may display a delay time until the change in the bladder 140 appears as the output value of each sensor of the oxygen measurement device 10A or 10B on the monitor 114.

The monitor main body portion 94 allows the user to set predetermined conditions. The monitor main body portion 94 may determine and notify whether or not a state in which the setting condition is satisfied has elapsed for a set time. That is, for example, in a case where urine of the set urine volume cannot be acquired, the monitor main body portion 94 may notify when a state where setting conditions are satisfied (the low output state of the sensor, the state where the temperature in the bladder 140 is lower than the setting temperature, and the like) continues for the set time or more.

The monitor main body portion 94 may determine and notify that the set change has occurred. That is, for example, the monitor main body portion 94 may notify when the rate of change in the flow rate of urine exceeds the set rate of change or when the range of change in the measured temperature of urine exceeds the set range of change.

The monitor main body portion 94 may have a function of maintaining the program inside, and may be configured to be able to update the program by receiving update information from the outside. In this case, the monitor main body portion 94 may receive the update information by wireless connection or wired connection (USB connection) with respect to the update information supply source. In addition, the monitor main body portion 94 may receive update information by replacing the memory card.

The monitor main body portion 94 may be configured to easily operate necessary functions. That is, the monitor main body portion 94 may be configured to have at least one physical function key and to freely assign functions to each function key. For example, the monitor main body portion 94 may be configured to be able to perform retroactive operation on past data by performing a dial operation or a slide operation of the monitor 114 (screen).

The monitor main body portion 94 may be configured to be able to print data in a selected range from an external printer or the like.

The monitor main body portion 94 may be configured to be able to divide a display area of the monitor 114 and display any data in each display area. In this case, for example, current data and past data can be easily compared. The monitor main body portion 94 may be configured to be able to output and display the display of the monitor 114 on an external display apparatus.

The monitor main body portion 94 may be configured to estimate a range of a urine volume from an infusion volume, and, at the same time, to compare the estimated range and an actual urine volume; to determine whether or not the urine volume range is within the estimated range; and to report the determination results. The infusion volume may be acquired by automatically obtaining infusion data from an infusion pump, or may be acquired by directly inputting the infusion volume.

The detailed description above describes embodiments of a monitoring system and an oxygen measurement system representing examples of the inventive monitoring system and an oxygen measurement system disclosed here. The invention is not limited, however, to the precise embodiments and variations described. Various changes, modifications and equivalents can be affected by one skilled in the art without departing from the spirit and scope of the invention as defined in the accompanying claims. It is expressly intended that all such changes, modifications and equivalents which fall within the scope of the claims are embraced by the claims.

What is claimed is:

1. An oxygen measurement system comprising:
   a urethral catheter that includes a urine flow lumen in which urine flows;
   an oxygen sensor that is mounted along the urine flow lumen in the urethral catheter and that outputs an output signal used to calculate an oxygen partial pressure in the urine flowing in the urine flow lumen of the urethral catheter;
   a flow rate sensor that is mounted along the urine flow lumen in the urethral catheter and that outputs an output signal used to calculate a flow rate of the urine flowing in the urine flow lumen of the urethral catheter;
   a control unit that is configured to calculate the oxygen partial pressure in the urine flowing in the urine flow lumen of the urethral catheter based on the output signal output from the oxygen sensor;
   the control unit being configured to calculate, while the urine is flowing in the urine flow lumen of the urethral catheter, the flow rate of the urine flowing in the urine flow lumen of the urethral catheter based on the output signal output from the flow rate sensor;
   a monitor that displays the calculated oxygen partial pressure; and
   the control unit being connected to the monitor and configured to change a format of a display of the oxygen partial pressure on the monitor based on the calculated flow rate of the urine while the urine is flowing in the urine flow lumen so that the oxygen partial pressure is displayed on the monitor in one format when the calculated flow rate of the urine while the urine is flowing in the urine flow lumen is a first calculated value and is displayed on the monitor in another visually distinguishable format when the calculated flow rate of the urine while the urine is flowing in the urine flow lumen is a second calculated value different from the first calculated value.

2. The oxygen measurement system according to claim 1, wherein the control unit is configured to:
   determine whether or not the calculated flow rate of the urine based on the output signal from the flow rate sensor is equal to or more than a predetermined value;
   display the oxygen partial pressure on the monitor in the one format when the first calculated value of the flow rate of the urine is equal to or greater than the predetermined value; and
   display the oxygen partial pressure on the monitor in the other visually distinguishable format when the second calculated value of the flow rate of the urine is less than the predetermined value.

3. The oxygen measurement system according to claim 1, wherein the display of the oxygen partial pressure on the monitor is a graph indicating a temporal change of the oxygen partial pressure, a portion of the graph being displayed in the one format when the calculated flow rate of the urine while the urine is flowing in the urine flow lumen is the first calculated value, and a different portion of the graph being displayed in the other visually distinguishable format when the calculated flow rate of the urine while the urine is flowing in the urine flow lumen is the second calculated value.

4. The oxygen measurement system according to claim 1, wherein the control unit is configured to calculate the oxygen partial pressure in the urine corrected by temperature of the urine based on an output signal from a further sensor.

5. The oxygen measurement system according to claim 1, wherein the control unit is:
   connected to the flow rate sensor to receive the output signal from the flow rate sensor and is configured to calculate, for display on the monitor, a urine volume based on the output signal from the flow rate sensor;

configured to determine whether or not the calculated urine volume matches a predetermined urine volume condition; and configured to display the predetermined urine volume condition on the monitor when the urine volume matches the predetermined urine volume condition.

6. The oxygen measurement system according to claim 1, wherein the calculated oxygen partial pressure is displayed on the monitor as a bar graph, and the one format is a filled part of the bar graph while the other visually distinguishable format is an unfilled part of the bar graph.

7. The oxygen measurement system according to claim 1, wherein the calculated oxygen partial pressure is displayed on the monitor as a line graph, and the one format is a first line of the line graph while the other visually distinguishable format is a second line of the line graph, the first line being thicker than the second line.

8. The oxygen measurement system according to claim 1, wherein the calculated oxygen partial pressure is displayed on the monitor as a line graph, the one format is a first line of the line graph with a portion of the line graph under the first line being a filled part, the other visually distinguishable format being a second line of the line graph with a portion of the line graph under the second line being unfilled.

9. A monitoring system that is connectable to a first sensor and a second sensor to be exposed to flowing urine that is flowing and which operates to calculate an oxygen partial pressure in the flowing urine that is flowing and a flow rate of the flowing urine that is flowing, the monitoring system comprising:

a monitor;

a control unit configured to be connected to the first sensor to receive an output signal from the first sensor and configured to calculate, for display on the monitor, the oxygen partial pressure in the flowing urine that is flowing based on the output signal from the first sensor;

the control unit being configured to be connected to the second sensor to receive an output signal from the second sensor and configured to calculate the flow rate of the flowing urine that is flowing based on the output signal from the second sensor; and the control unit being connected to the monitor and being configured to control a format of a display of the oxygen partial pressure on the monitor based on the calculated flow rate of the flowing urine that is flowing so that the oxygen partial pressure is displayed on the monitor in one format when the calculated flow rate of the flowing urine that is flowing is a first calculated value and is displayed on the monitor in an other visually distinguishable format when the calculated flow rate of the flowing urine that is flowing is a second calculated value different from the first calculated value.

10. The monitoring system according to claim 9, wherein the control unit is configured to:

determine whether or not the calculated flow rate of the urine based on the output signal from the second sensor is equal to or more than a predetermined value, display the oxygen partial pressure on the monitor in the one format when the first calculated value of the flow rate of the urine is equal to or greater than the predetermined value, and display the oxygen partial pressure on the monitor in the other visually distinguishable format when the second calculated value of the flow rate of the urine is less than the predetermined value.

11. The monitoring system according to claim 9, wherein the display of the oxygen partial pressure on the monitor is a graph indicating a temporal change of the oxygen partial pressure, a portion of the graph being displayed in the one format when the calculated flow rate of the flowing urine that is flowing is the first calculated value, and a different portion of the graph being displayed in the other visually distinguishable format when the calculated flow rate of the flowing urine that is flowing is the second calculated value.

12. The monitoring system according to claim 9, wherein the control unit calculates the oxygen partial pressure in the urine corrected by temperature of the urine based on an output signal from a further sensor.

13. The monitoring system according to claim 9, wherein:

the control unit is configured to be connected to the second sensor to receive the output signal from the second sensor and is configured to calculate, for display on the monitor, a urine volume based on the output signal from the second sensor;

the control unit is configured to determine whether or not the calculated urine volume matches a predetermined urine volume condition; and the control unit is configured to display the predetermined urine volume condition on the monitor when the urine volume matches the predetermined urine volume condition.

14. A method comprising:

positioning a distal portion of an elongated urethral catheter in a bladder of a living body, the elongated urethral catheter including a lumen extending along the elongated urethral catheter;

introducing urine from the bladder of the living body into the lumen of the elongated urethral catheter so that the urine is flowing in the lumen of the elongated urethral catheter;

calculating an oxygen partial pressure in the urine flowing in the lumen of the elongated urethral catheter based on an output signal of a first sensor that is contacted by the urine flowing in the lumen of the elongated urethral catheter;

calculating a flow rate of the urine flowing in the lumen of the elongated urethral catheter based on an output signal from a second sensor that is contacted by the urine flowing in the lumen of the elongated urethral catheter; and controlling a display of the calculated oxygen partial pressure on a monitor so that the calculated oxygen partial pressure is displayed on the monitor in one format when the calculated flow rate of the urine flowing in the lumen of the elongated urethral catheter is a first calculated value and is displayed on the monitor in an other visually distinguishable format when the calculated flow rate of the urine flowing in the lumen of the elongated urethral catheter is a second calculated value different from the first calculated value.

15. The method according to claim 14, further comprising:

determining whether or not the calculated flow rate of the urine in the lumen of the elongated urethral catheter is at least equal to a predetermined value;

displaying the calculated oxygen partial pressure on the monitor in the one format when the first calculated value of the flow rate of the urine is at least equal to the predetermined value; and displaying the calculated oxygen partial pressure on the monitor in the other visually distinguishable format when the second calculated value of the flow rate of the urine is less than the predetermined value.

16. The method according to claim 14, wherein the display of the calculated oxygen partial pressure on the monitor is a graph indicating a temporal change of the calculated oxygen partial pressure, a portion of the graph being displayed in the one format when the calculated flow rate of the urine flowing in the lumen of the elongated urethral catheter is the first calculated value, and a different portion of the graph being displayed in the other visually distinguishable format when the calculated flow rate of the urine flowing in the lumen of the elongated urethral catheter is the second calculated value.

17. The method according to claim 14, further comprising determining a temperature of the urine in the lumen of the elongated urethral catheter, and wherein the calculating of the oxygen partial pressure in the urine in the lumen of the elongated urethral catheter comprises calculating the oxygen partial pressure that is corrected by the temperature of the urine.

18. The method according to claim 14, further comprising:
- calculating a urine volume based on the output signal from the second sensor;
- determining whether or not the calculated urine volume matches a predetermined urine volume condition; and
- displaying the predetermined urine volume condition on the monitor when the urine volume is determined to match the predetermined urine volume condition.

* * * * *